United States Patent [19]

Kobayashi et al.

[11] Patent Number: 4,483,919

[45] Date of Patent: Nov. 20, 1984

[54] SILVER HALIDE PHOTOGRAPHIC LIGHT-SENSITIVE MATERIAL

[75] Inventors: Hidetoshi Kobayashi; Isamu Itoh; Yasuhiro Yoshioka; Keiji Mihayashi; Noriyuki Inoue, all of Kanagawa, Japan

[73] Assignee: Fuji Photo Film Co., Ltd., Kanagawa, Japan

[21] Appl. No.: 564,659

[22] Filed: Dec. 23, 1983

[30] Foreign Application Priority Data

Dec. 28, 1982 [JP] Japan ................................. 57-229849

[51] Int. Cl.$^3$ ............................................... G03C 1/02
[52] U.S. Cl. ..................................... 430/566; 430/218; 430/440; 430/483; 430/443; 430/959
[58] Field of Search ............... 430/566, 443, 959, 955, 430/218, 440, 483, 480

[56] References Cited

U.S. PATENT DOCUMENTS

| | | | |
|---|---|---|---|
| 3,597,203 | 8/1971 | Willems | 430/566 |
| 4,266,002 | 5/1981 | McCreary et al. | 430/959 |
| 4,330,617 | 5/1982 | Ohashi et al. | 430/566 |
| 4,409,324 | 10/1983 | Ishikawa et al. | 430/566 |

*Primary Examiner*—Mary F. Downey
*Attorney, Agent, or Firm*—Sughrue, Mion, Zinn, Macpeak & Seas

[57] ABSTRACT

A silver halide photographic light-sensitive material containing at least one compound represented by the general formula (I):

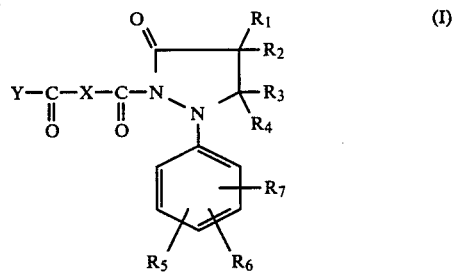

is disclosed. The compound of the invention has good stability over time. The material has improved developability and makes it possible to carry out simple and rapid processing. The material has good resistance with respect to fogging, stains and desensitization.

9 Claims, No Drawings

SILVER HALIDE PHOTOGRAPHIC LIGHT-SENSITIVE MATERIAL

FIELD OF THE INVENTION

This invention relates to a silver halide photographic light-sensitive material with improved developability and, more particularly, to a silver halide photographic light-sensitive material with improved developability containing a developing agent precursor having good stability with time.

BACKGROUND OF THE INVENTION

An image-forming process using silver halide photographic light-sensitive materials generally involves the main steps of development, fixing (or bleaching and fixing), and the like. In the developing step, developing agents well known in the art (for example, compounds as described in *The Theory of the Photographic Processes*, 4th Ed., compiled by T. H. James, pp. 298-324) dissolved in an alkaline aqueous solution are usually used as developing solutions.

Such developing solutions are unstable and are easily oxidized with dissolved oxygen or the like. Therefore, preservatives are added thereto to prevent oxidation. However, the developing solutions are so unstable in composition that their preservation is difficult. Recently, therefore, a technique of incorporating a developing agent in a silver halide light-sensitive material has been proposed.

Incorporation of a developing agent in a light-sensitive material makes it possible to simplify the composition of a processing solution. This facilitates the aforesaid preservation of a developing solution and is, in addition, advantageous for simplifying or accelerating the processing because the development can be fundamentally conducted in an alkaline bath.

Therefore, it has conventionally been attempted to incorporate a developing agent in a light-sensitive material. For example, photographic elements in which a black-and-white developing agent is incorporated in a light-sensitive material are described in U.S. Pat. Nos. 2,751,297, 3,902,905, 4,209,580, etc.

In general, however, incorporation of a developing agent as such in a light-sensitive material causes the developing agent to be oxidized in a comparatively short time. Further, problems such as desensitization, fogging, staining, etc., are liable to be caused during storage of the light-sensitive material and the developing agent loses its power to give only insufficient image density.

One technique proposed for removing these defects is to incorporate a developing agent precursor in a light-sensitive material. This precursor does not possess developing power during storage, and, hence, does not undergo oxidation and, only when brought into contact with a suitable activator (for example, alkalis, nucleophilic reagents, etc.), it produces a silver halide developing agent.

As such precursors, U.S. Pat. No. 3,295,978 describes salts of metals (lead, cadmium, calcium, barium, etc.) of hydroquinone, catechol, etc., U.S. Pat. No. 3,246,988 describes acyl halide derivatives of hydroquinone, U.S. Pat. No. 3,462,266 describes oxazine derivatives of hydroquinone, U.S. Pat. No. 3,615,512 describes lactone type developing agent precursors, British Pat. No. 1,258,924 describes hydroquinone presursors having a quaternary ammonium group, and British Pat. No. 1,023,701 describes acyl derivatives of 1-phenyl-3-pyrazolidinone.

However, these conventional developing agent precursors have the defect that some of them gradually release a developing agent during storage which is then oxidized, making it less effective, causing desensitization or fogging or to form a colored product, and others undergo a too slow decomposition upon desired development to produce a developing agent, thus having been unsatisfactory. That is, conventional developing agent precursors do not fully satisfy the following two requirements:

(1) Sufficiently stable against decomposition and oxidative deterioration during storage not to release a developing agent or form other compound; and (2) capable of releasing a developing agent upon desired development processing in a short time in comparison with the developing time.

SUMMARY OF THE INVENTION

It is, therefore, an object of the present invention to provide a silver halide photographic light-sensitive material which has improved developability, and which allows simple and rapid processing.

Another object of the present invention is to provide a silver halide photographic light-sensitive material which has extremely good stability with time against fogging, desensitization and staining.

A further object of the present invention is to provide a silver halide light-sensitive material having high sensitivity.

Still a further object of the present invention is to provide a silver halide light-sensitive material which provides high image density.

These objects of the present invention have been successfully attained by a silver halide photographic light-sensitive material containing at least one compound represented by the following general formula (I):

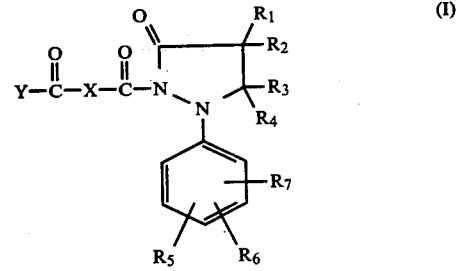

wherein $R_1$ and $R_2$ each independently represent a hydrogen atom or an alkyl group; $R_3$ and $R_4$ each independently represent a hydrogen atom, an alkyl group, an alkoxycarbonyl group or an aryl group; $R_5$, $R_6$ and $R_7$ each independently represent a hydrogen atom, a halogen atom, an alkyl group, an alkoxy group, an aryl group, a carbonamido group or a sulfonamido group; X represents a divalent linkage group represented by the following general formula (II) or (III):

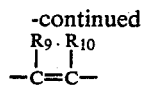
(III)

wherein R₈ represents a hydrogen atom, an alkyl group, an alkenyl group, an aryl group, a halogen atom, an alkoxy group or an alkylthio group; R₉ and R₁₀ each independently represent a hydrogen atom, a halogen atom, an alkyl group or an aryl group, provided R₉ and R₁₀ may jointly form a benzene ring; and n represents an integer of 2 or 3;

and Y represents —OH,

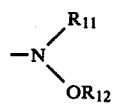

or R₁₃ wherein R₁₁ represents a hydrogen atom, an aryl group or an alkyl group; R₁₂ represents a hydrogen atom or an acyl group; and R₁₃ represents a hydrolyzable group.

DETAILED DESCRIPTION OF THE INVENTION

The reaction according to which the developing agent precursors release a 1-phenyl-3-pyrazolidinone seems to proceed as follows. For example, with the precursors of the general formula (I) wherein Y represents —OH or —R₁₃, the reaction proceeds as follows:

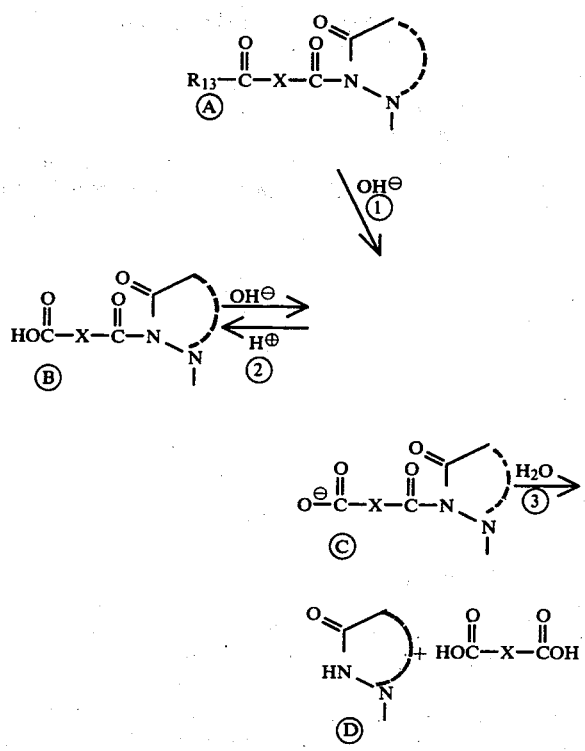

The developing agent precursors of the present invention are dispersed into a photographic layer in the form of Ⓐ or Ⓑ. During storage, equilibrium of reaction ② which produces carboxyl anion predominantly proceeds to produce precursor Ⓑ, because the OH⁻ ion concentration is as low as $10^{-7}$ to $10^{-3}$ times as much as that upon development. This predominance of equilibrium becomes greater where the precursor is dissolved in an organic phase such as a high-boiling organic solvent or a high molecular weight solvent in a separate form from an aqueous or hydrophilic phase. In addition, during storage, developing agent precursor Ⓐ or Ⓑ has such a low solubility in a corresponding neutral and/or acidic aqueous solution that, where an organic phase exists, it is mostly distributed in the organic phase. Further, since the water concentration during storage is smaller than that upon development, hydrolysis reaction ① and sequent reaction ③ take place with difficulty and, therefore, the developing agent precursors of the present invention stably exist during storage.

On the other hand, when a silver halide photographic light-sensitive material containing the developing agent precursor of the present invention is brought into contact with an alkaline developing solution, carboxyl anion Ⓒ is rapidly produced by the hydrolysis reaction ① or equilibrium reaction ②. The carboxyl anion Ⓒ has such high solubility in an alkaline aqueous solution that it is distributed into the developing solution, thus being easily hydrolyzed. The same applies to the developing agent precursors wherein Y represents

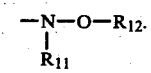

Therefore, the developing agent precursors of the present invention have the characteristic aspects that they are stable during storage and that, upon development processing, they release a developing agent in an extremely short time.

A further aspect of the developing agent precursors of the present invention is that they can be synthesized extremely easily as is shown by the Synthesis Examples to be described hereinafter.

Where R₁ and R₂ in the general formula (I) represent alkyl groups, they preferably contain 1 to 18 carbon atoms, and examples thereof include a methyl group, an ethyl group, a hydroxymethyl group, a hydroxyethyl group, a chloromethyl group, an acetoxymethyl group, a benzoyloxymethyl group, a tetradecanoyloxymethyl group, etc.

Where R₃ and R₄ represent alkyl groups, they preferably contain 1 to 12 carbon atoms, and examples thereof include a methyl group, an ethyl group, etc. Where they represent alkoxycarbonyl groups, they preferably contain up to 13 carbon atoms, and examples thereof include a methoxycarbonyl group, an ethoxycarbonyl group, a hexyloxycarbonyl group, etc. Where they represent aryl groups, they preferably contain up to 13 carbon atoms, and examples thereof include a phenyl group, a 4-methoxyphenyl group, a 2-methoxyphenyl group, a 2-hydroxyphenyl group, a 4-chlorophenyl group, a 3-butoxyphenyl group, etc.

Where R₅, R₆ and R₇ represent alkyl groups, they preferably contain up to 12 carbon atoms, and examples thereof include a methyl group, an ethyl group, and a dodecyl group. Where they represent alkoxy groups, they preferably contain up to 16 carbon atoms, and examples thereof include a methoxy group, an ethoxy group, a butoxy group, a hexadecyloxy group, a methoxyethoxy group, a butoxyethoxy group, etc. Where they represent aryl groups, they preferably contain up to 12 carbon atoms, and examples thereof include a phenyl group and a p-tolyl group, etc. Where they represent carbonamido groups, examples thereof include an acetamido group, etc., and where they represent sulfonamido groups, examples thereof include a methanesulfonamido group, etc. Further, where they represent halogen atoms, examples thereof include a fluorine atom, a chlorine atom, a bromine atom, etc.

Where $R_{11}$ represents an alkyl group, it preferably contains up to 24 carbon atoms, and examples thereof include a methyl group, an isopropyl group, a dodecyl group, etc. Where it represents an aryl group, it preferably contains up to 18 carbon atoms, and examples thereof include a phenyl group, a 4-methoxyphenyl group, a 2-chlorophenyl group, a 4-methylphenyl group, etc.

Where $R_{12}$ represents an acyl group, examples thereof include an acetyl group, a benzoyl group, a p-nitrobenzoyl group, etc.

Examples of hydrolyzable group represented by $R_{13}$ include a phenoxy group, a 4-chlorophenoxy group, a 4-nitrophenoxy group, a 2,4-dinitrophenoxy group, a 2,2,2-trifluoroethoxy group, a 2-cyanoethoxy group, a 2,2,2-trichloroethoxy group, a 2,2-dichloroethoxy group, etc.

Where $R_8$ in the general formula (II) represents an alkyl group, it preferably contains up to 24 carbon atoms, and examples thereof include a methyl group, a dodecyl group, etc. Where it represents an alkenyl group, it preferably contains up to 24 carbon atoms, and examples thereof include an octadecenyl group, etc. Where it represents an aryl group, it preferably contains up to 24 carbon atoms, and examples thereof include a phenyl group, a 4-dodecylphenyl group, etc. Where it represents an alkoxy group, it preferably contains up to 24 carbon atoms, and examples thereof include a methoxy group and a dodecyloxy group, etc. Where it represents an alkylthio group, etc., it preferably contains up to 24 carbon atoms, and examples thereof include a methylthio group, a dodecylthio group, etc. Further, where it represents a halogen atom, examples thereof include a fluorine atom, a chlorine atom, a bromine atom, etc.

Where $R_9$ and $R_{10}$ in the general formula (III) represent alkyl groups, they preferably contain up to 24 carbon atoms, and examples thereof include a methyl group, an octyl group, etc. Where they represent aryl groups, they preferably contain up to 24 carbon atoms, and examples thereof include a phenyl group, a 4-methoxyphenyl group, etc. Further, where they represent halogen atoms, examples thereof include a fluorine atom, a chlorine atom, a bromine atom, etc.

Specific examples of the compounds of the present invention are illustrated below.

Compound Examples

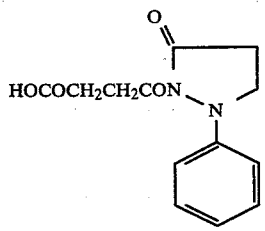
(1)

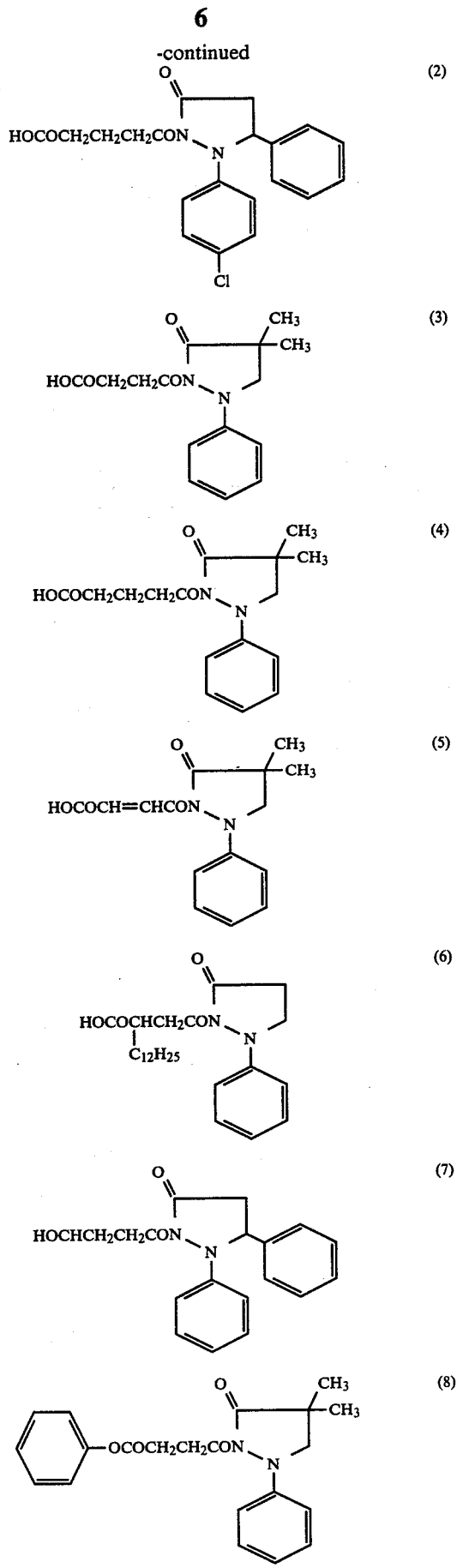

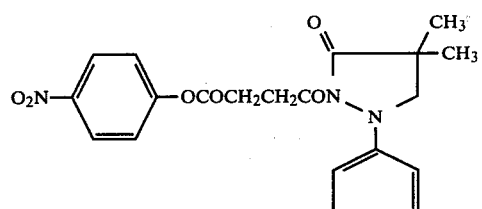 (9)

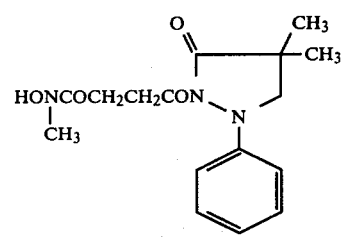 (10)

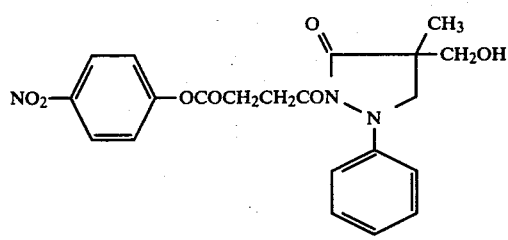 (11)

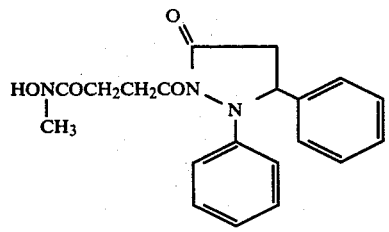 (12)

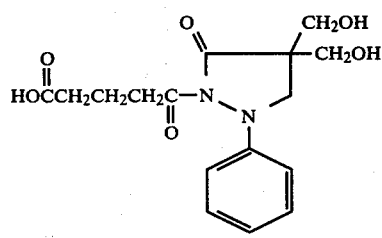 (13)

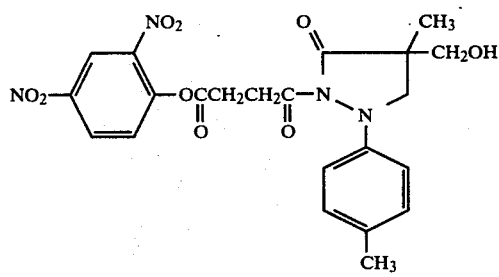 (14)

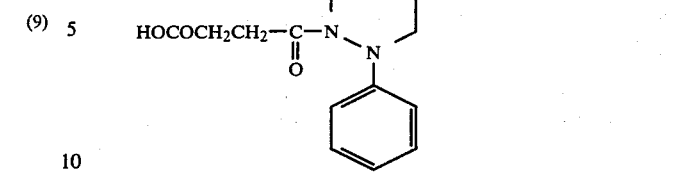 (15)

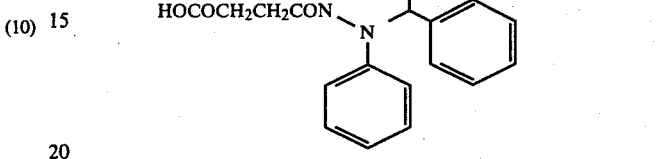 (16)

The compounds of the present invention represented by the general formula (I) can be easily obtained by reacting a 1-phenyl-3-pyrazolidinone and an acid anhydride with a base (for example, triethylamine, N-ethylmorpholine, diazabicycloundecene (DBU), diazabicyclononane (DBN), etc.) in an organic solvent such as tetrahydrofuran, ethyl acetate, dioxane, acetonitrile, chloroform, methylene chloride, etc. The structures of the synthesized compounds of the present invention were identified through infrared absorption spectrum, UV ray absorption spectrum, proton nuclear magnetic resonance spectrum, and $^{13}C$ nuclear magnetic resonance spectrum. For obtaining more assuring data, enol acetates of 1-phenyl-2-acetyl-3-pyrazolidinone and 1-phenyl-3-pyrazolidinone were synthesized as model compounds according to the process described in British Pat. No. 1,023,701, and various spectral data of these compounds were compared to that of the present invention, thus the structures of the latter compounds being identified. Synthesis Examples will be described below.

SYNTHESIS EXAMPLE 1

Synthesis of Compound Example (1)

16.2 g of 1-phenyl-3-pyrazolidinone and 11 g of succinic anhydride were dissolved in 100 ml of tetrahydrofuran and, under stirring at 25° C., 11.3 g of triethylamine was gradually added dropwise thereto. After completion of the dropwise addition, stirring was further continued for 3 hours, and the reaction solution was then concentrated under reduced pressure. The residue was dissolved in 30 ml of water, neutralized with concentrated hydrochloric acid, and then extracted with ethyl acetate. The ethyl acetate solution was concentrated, and the residue was purified by column chromatography using n-hexane/ethyl acetate as a developing solvent to obtain 10.2 g of oily end compound (1). Yield: 39%.

Elemental Analysis:

|  | C (%) | H (%) | N (%) |
|---|---|---|---|
| Calcd. for $C_{15}H_{18}N_2O_4$: | 59.54 | 5.38 | 10.68 |
| Found: | 59.43 | 5.41 | 10.62 |

SYNTHESIS EXAMPLE 2

Synthesis of Compound Example (3)

28.5 g of 1-phenyl-4,4-dimethyl-3-pyrazolidinone and 16.5 g of succinic anhydride were dissolved in 150 ml of tetrahydrofuran and, under stirring at 25° C., 16.7 g of triethylamine was added dropwise thereto in 1 hour. After completion of the dropwise addition, stirring was further continued for 5 hours, and the reaction solution was concentrated. 300 ml of ethyl acetate was added to the residue for dissolution. The ethyl acetate solution was washed with dilute hydrochloric acid and then concentrated. Crystallization of the residue from an n-hexane/ethyl acetate mixed solvent gave 25.8 g of end compound (3). Yield: 59%; m.p. 125°–126° C.

Elemental Analysis:

|  | C (%) | H (%) | N (%) |
|---|---|---|---|
| Calcd. for $C_{13}H_{14}N_2O_4$: | 62.06 | 6.25 | 9.65 |
| Found: | 62.01 | 6.33 | 9.43 |

SYNTHESIS EXAMPLE 3

Synthesis of Compound Example (4)

9.5 g of 1-phenyl-4,4-dimethyl-3-pyrazolidinone and 6.3 g of glutaric anhydride were dissolved in 45 ml of tetrahydrofuran and, under stirring at 25° C., 6.2 g of triethylamine was added dropwise thereto in 30 minutes. After completion of the dropwise addition, stirring was further continued for 5 hours, and the reaction solution was concentrated. The residue was dissolved in 100 ml of ethyl acetate, washed with dilute hydrochloric acid, and then concentrated to obtain an oily product. Crystallization of the product from an n-hexane/isopropanol mixed solvent yielded 8.2 g of end compound (4). Yield: 54%; m.p. 97°–98° C.

Elemental Analysis:

|  | C (%) | H (%) | N (%) |
|---|---|---|---|
| Calcd. for $C_{16}H_{20}N_2O_4$: | 63.15 | 6.62 | 9.20 |
| Found: | 63.24 | 6.68 | 9.31 |

SYNTHESIS EXAMPLE 4

Synthesis of Compound Example (7)

11.9 g of 1,5-diphenyl-3-pyrazolidinone and 5.5 g of succinic anhydride were dissolved in 150 ml of tetrahydrofuran and, under stirring at 25° C., 5.7 g of triethylamine was added dropwise thereto in 30 minutes. After completion of the dropwise addition, stirring was further continued for 30 minutes, and the reaction solution was concentrated. The residue was dissolved in 50 ml of ethyl acetate. The ethyl acetate solution was washed with dilute hydrochloric acid and then concentrated. The residue was purified by column chromatography using n-hexane/ethyl acetate as a developing solution to obtain 6.8 g of end compound (7). Yield: 40%.

Elemental Analysis:

|  | C (%) | H (%) | N (%) |
|---|---|---|---|
| Calcd. for $C_{19}H_{18}N_2O_4$: | 67.45 | 5.36 | 8.28 |
| Found: | 67.32 | 5.44 | 8.24 |

SYNTHESIS EXAMPLE 5

Synthesis of Compound Example (8)

14.5 g of compound example (3), 4.9 g of phenol, and 0.2 g of 4-dimethylaminopyridine were dissolved in 150 ml of acetonitrile, and a solution of 10.3 g of dicyclohexylcarbodiimide in 10 ml of acetonitrile was added dropwise thereto in 30 minutes under stirring. After completion of the dropwise addition, stirring was continued for 1 hour at 25° C., then for 1 hour at 50° C. After allowing the reaction solution to cool, it was filtered. The filtrate was concentrated, and the obtained oily product was crystallized from an n-hexane/ethyl acetate mixed solvent to obtain 11.7 g of end compound (8). Yield: 11.7 g; m.p. 120°–122° C.

Elemental Analysis:

|  | C (%) | H (%) | N (%) |
|---|---|---|---|
| Calcd. for $C_{21}H_{22}N_2O_4$: | 68.84 | 6.05 | 7.65 |
| Found: | 68.72 | 6.04 | 7.58 |

The developing agent precursors of the present invention may be used in combination of two or more.

The developing agent precursors of the present invention may be added to any of a silver halide emulsion layer, colorant layer, subbing layer, protective layer, interlayer, filter layer, antihalation layer, image-receiving layer, cover sheet layer, and other auxiliary layers of a silver halide photographic light-sensitive material.

The developing agent precursors can be added to these layers by adding them to coating solutions for forming the photographic layers as they are or as a solution of a solvent not adversely affecting the silver halide photographic light-sensitive material, such as water or alcohols, in a suitable concentration. In addition, the developing agent precursors may be added to the layers by dissolving them in a high-boiling or low-boiling organic solvent and emulsifying and dispersing the solution in an aqueous solution. Further, they may be added to the layers by impregnating in a polymer latex as described in Japanese Patent Application (OPI) Nos. 39853/76, 59942/76 and 32552/79, U.S. Pat. No. 4,199,363, etc. (the term "OPI" as used herein refers to a "published unexamined Japanese patent application").

The developing agent precursor may be added in any stage of the process of manufacturing photographic materials but, in general, it is preferably added immediately before the coating stage. The amount of the developing agent precursor to be added is suitably $10^{-9}$ mol to $10^{-1}$ mol per m² of a silver halide photographic light-sensitive material, with $10^{-7}$ mol to $10^{-2}$ mol being preferable.

The compounds of the present invention can be used in, for example, coupler system color photographic light-sensitive materials.

The general process for forming a color image from a color photographic light-sensitive material is a process of producing azomethine or indoaniline dyes by developing a silver halide light-sensitive material with an aromatic primary amine in the presence of color couplers capable of reacting with an oxidation product of the developing agent to form dyes. This color developing process was fundamentally invented in the year 1935 by L. D. Mannes & L. Godowsky. Since then, various improvements of the process have been made and, now, it is being employed throughout the world. In this process, a subtractive process is usually used for reproducing colors. Thus, silver halide emulsions selectively responding to blue, green and red are used in association with yellow, magenta and cyan color image-forming agents, respectively, the colors to be formed by the color image-forming agents being in a complementary relation with blue, green and red, respectively. For example, acylacetanilide or dibenzoylmethane type couplers are used for forming yellow color images. Pyrazolone, pyrazolobenzimidazole, cyanoacetophenone or indazolone type couplers are mainly used for forming magenta color images, and phenolic couplers such as phenols and naphthols are mainly used for forming cyan color images.

Usually, color photographic light-sensitive materials are roughly categorized into two groups: one being a coupler-free type (couplers being contained in a developing solution); and the other being coupler-incorporated type in which couplers are contained separately in each light-sensitive layer of the light-sensitive material so as to keep their independent functions. In the latter type, couplers forming dye images are added to a silver halide emulsion. The couplers to be added to the emulsion must be rendered non-diffusible (diffusion-resistant) in an emulsion binder matrix.

Processing steps of the coupler-incorporated type light-sensitive materials are fundamentally composed of the following three steps:

(1) color developing step;
(2) bleaching step; and
(3) fixing step.

The bleaching step and the fixing step may be conducted at the same time. Such step is a bleach-fixing step (called blix), in which developed silver and undeveloped silver halide are desilvered. Actual development processing involves, in addition to the above-described two fundamental steps of color development and desilvering, auxiliary steps for maintaining photographic and physical quality of formed images or for improving preservability of images. For example, there are illustrated a hardening bath for preventing light-sensitive films from being softened too much during processing, a stopping bath for effectively stopping development reaction, an image-stabilizing bath for stabilizing images, a film-removing bath for removing a backing layer from the support, etc.

Conventionally known methods for adding to or emulsifying in an emulsion a coupler and for adding the emulsion to a gelatin/silver halide emulsion or a hydrophilic colloid can be employed. For example, there can be employed a method of mixing a coupler with a high-boiling organic solvent (e.g., dibutyl phthalate, tricresyl phosphate, wax, higher fatty acid, its ester, etc.) to disperse as described in, for example, U.S. Pat. Nos. 2,304,939 and 2,322,027, etc., a method of intimately mixing a coupler with a low-boiling organic solvent or a water-soluble organic solvent for dispersion, and a method of dispersing a coupler by using both a low-boiling or water-soluble organic solvent and a high-boiling organic solvent as described in, for example, U.S. Pat. Nos. 2,801,170, 2,801,171 and 2,949,360, etc. With couplers which themselves have an enough low melting point (for example, not higher than 75° C.), they may be dispersed alone or in combination with other couplers to be used in combination (for example, colored couplers or uncolored couplers) as described in German Pat. No. 1,143,707.

As dispersing aids, usually used anionic surfactants (for example, sodium alkylbenzenesulfonates, sodium dioctyl sulfosuccinates, sodium dodecylsulfates, sodium alkylnaphthalenesulfonates, Fischer type couplers, etc.), amphoteric surfactants (for example, N-tetradecyl-N,N-dipolyethylene α-betaine, etc.), and nonionic surfactants (for example, sorbitan monolaurate, etc.) are employed.

Specific examples of magenta color couplers are those described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,310,464, West German Offenlegungsschrift Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76, and 55122/78, etc.

Specific examples of yellow color couplers are those described in U.S. Pat. Nos. 2,875,057, 3,265,506, 3,408,194, 3,551,155, 3,582,322, 3,725,072 and 3,891,445, West German Pat. No. 1,547,868, West German Offenlegungsschrift Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77, etc.

Specific examples of cyan color couplers are those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, and 3,767,411, 4,004,929, West German Offenlegungsschrift Nos. 2,414,830 and 2,454,329, Japanese Patent Application (OPI) Nos. 59838/73, 26034/76, 5055/73, 146828/76, 69624/77 and 90932/77, etc.

As colored couplers, those described in, for example, U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, and West German Offenlegungsschrift No. 2,418,959 can be used.

As DIR couplers, those described in, for example, U.S. Pat. Nos. 3,227,554, 3,617,291, 3,701,783, 3,790,384 and 3,632,345, West German Offenlegungsschrift Nos. 2,414,006, 2,454,301 and 2,454,329, British Pat. No. 953,454, Japanese Patent Application (OPI) Nos. 69624/77 and 122335/74, and Japanese Patent Publication No. 16141/76 can be used.

In addition to the DIR couplers, compounds capable of releasing development restrainers upon development may be incorporated in the light-sensitive material. For example, those described in U.S. Pat. Nos. 3,297,445 and 3,379,529, West German Offenlegungsschrift No. 2,417,914, Japanese Patent Application (OPI) Nos. 15271/77 and 9116/78 can be used.

High-boiling organic solvents to be used are described in, for example, U.S. Pat. Nos. 2,322,027, 2,533,514 and 2,835,579, Japanese Patent Publication No. 23233/71, U.S. Pat. No. 3,287,134, British Pat. No. 958,441, Japanese Patent Application (OPI) No. 1031/72, British Pat. No. 1,222,753, U.S. Pat. No. 3,936,303, Japanese Patent Application (OPI) Nos. 26037/76 and 82078/75, U.S. Pat. Nos. 2,353,262, 2,852,383, 3,554,755, 3,676,137, 3,676,142, 3,700,454, 3,748,141 and 3,837,863, West German Offenlegungsschrift No. 2,538,889, Japanese Patent Application (OPI) Nos. 27921/76, 27922/76, 26035/76, 26036/76 and 62632/75, Japanese Patent Publication No. 29461/74, Japanese Patent Application (OPI) No. 1521/78, etc.

The compounds of the present invention can also be used in various types of instant photography, for example, the type of using dye developers disclosed in U.S. Pat. Nos. 3,134,764, 3,173,929, 3,929,848 and 3,706,557, etc., the type of releasing diffusible dyes disclosed in U.S. Pat. Nos. 4,076,529, 4,135,929, 4,013,635, etc., and the like.

The compounds of the present invention can also be used for the type based on a silver dye bleaching process as described in "The Theory of the Photographic Process, Chapter 12, Principles and Chemistry of Color Photography IV, Silver Dye Bleach Process", 4th Ed., T. H. James ed., Macmillan, New York, 1977, pp. 363-366.

The compounds of the present invention can further be used in black-and-white light-sensitive materials. As such black-and-white light-sensitive materials, there are illustrated X-ray films for medical use, black-and-white films for general photographing use, lithographic films, scanner films, etc.

Other constitutions of the silver halide photographic light-sensitive material of the present invention, such as process for preparing a silver halide emulsion, composition of silver halide, crystal habit and grain size of silver halide, chemically sensitizing agent, antifogging agent, stabilizer, surfactant, gelatin hardener, hydrophilic colloid binder, matting agent, dye, sensitizing dye, anti-fading agent, color stain-preventing agent, polymer latex, bleaching agent, anti-static agent, etc., are not particularly limited, and reference can be made to the description of, for example, *Research Disclosure*, 176, pp. 22-31 (Dec., 1978).

In addition, the method for exposing the silver halide photographic light-sensitive material of the present invention, the method for developing it, etc., are not particularly limited. Any known methods and known processing solutions as described in *Research Disclosure*, 176, pp. 28-30 (Dec., 1978) can be applied. The photographic processing may be a black-and-white photographic processing for forming a silver image or a color photographic processing for forming a dye image depending upon the purpose. Processing temperature is usually selected between 18° to 50° C. However, temperatures lower than 18° C. or higher than 50° C. may be employed.

The developing solution for conducting black-and-white photographic processing can contain known developing agents. As the developing agents, dihydroxybenzenes (e.g., hydroquinone), 3-pyrazolidinones (e.g., 1-phenyl-3-pyrazolidinone), aminophenols (e.g., N-methyl-p-aminophenol), etc., can be used alone or in combination. Generally, the developing solution further contains known preservatives, alkali agents, pH buffers, antifogging agents, etc., and, if desired, may further contain dissolving aids, toning agents, development accelerators, surfactants, defoaming agents, water-softening agents, hardeners, thickeners, etc.

So-called "lith-type" development processing may be applied to the photographic emulsion of the present invention. "Lith-type" development processing means a development processing which generally uses a dihydroxybenzene as a developing agent and conducts development in an infectious manner at a low sulfite ion concentration for photographically reproducing line images or halftone dot images. (Detailed descriptions are given in Mason, *Photographic Processing Chemistry*, pp. 163-165 (1966).)

In forming dye images, ordinary processes can be applied. For example, there may be employed a negative-positive process (described in, for example, *Journal of the Society of Motion Picture and Television Engineers*, Vol. 61 (1953), pp. 667-701); a color reversal process of forming a negative silver image by developing with a developing solution containing a black-and-white developing agent, conducting at least one uniform exposure or other proper fogging processing, and subsequently conducting color development to thereby obtain positive dye images; a silver dye-bleaching process of developing a silver image by developing a dye-containing photographic emulsion layer after imagewise exposure to thereby form a silver image, and bleaching the dye using the silver image as a bleaching catalyst; and the like.

A color developing solution generally comprises an alkaline aqueous solution containing a color-developing agent. As the color-developing agent, known primary aromatic amine developing agents such as phenylenediamines (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-$\beta$-methanesulfonamidoethylaniline, 4-amino-3-methyl-N-ethyl-N-$\beta$-methoxyethylaniline, etc.) can be used.

In addition, those described in L. F. A. Mason, *Photographic Processing Chemistry* (Focal Press, 1966), pp. 226-229, U.S. Pat. Nos. 2,193,015 and 2,592,364, Japanese Patent Application (OPI) No. 64933/73, etc., can be used.

Usually, the photographic emulsion layer which has been subjected to color development processing is then bleached. This bleaching processing may be conducted simultaneously with fixing processing or may be conducted independently. As bleaching agents, compounds of polyvalent metals such as iron (III), cobalt (III), chromium (VI), copper (II), etc., peracids, quinones, nitroso compounds, etc., are used.

The present invention will now be described in more detail by the following non-limiting examples.

EXAMPLE 1

In order to evaluate the effectiveness of the developing agent precursors of the present invention in comparison with control (comparative) compounds, developing agents or precursors thereof given in Table 1 were dissolved in tricresyl phosphate to emulsify together with magenta coupler $C_{p-1}$, and added to emulsions to prepare emulsion layers, followed by coating each of the thus prepared emulsion layers on a subbed cellulose triacetate film support to prepare samples 1 to 10. The amounts of respective substances coated were indicated in parentheses as numerical values in terms of $g/m^2$ or $mol/m^2$.

(1) Emulsion Layer
  Negative type silver iodobromide emulsion (grain size: 1.5$\mu$) (silver: $1.6 \times 10^{-2}$ mol/m$^2$)
  Magenta coupler $C_{p-1}$ ($1.33 \times 10^{-3}$ mol/m$^2$)
  Developing agent or its precursor ($1.33 \times 10^{-3}$ mol/m$^2$)
  Gelatin (2.50 g/m$^2$)
(2) Protective Layer
  Gelatin (1.30 g/m$^2$)
  2,4-Dichloro-6-hydroxy-s-triazine sodium salt (50 mg/m$^2$)

These films were left for 14 hours at 40° C. and 70% RH, then imagewise exposed for conducting sensitometry and subjected to the following color development processing.

| Color Development Processing Step | Time (min) | Temperature (°C.) |
|---|---|---|
| 1. Color development | 3.25 | 38 |
| 2. Bleaching | 6.50 | " |
| 3. Washing with water | 2 | " |
| 4. Fixing | 4 | " |
| 5. Washing with water | 4 | " |
| 6. Stabilization | 1 | " |

The compositions of the processing solutions used in the color development processing steps are as follows:

| Color Developing Solution | |
|---|---|
| Water | 800 ml |
| 4-(N—Ethyl-N—hydroxyethyl)amino-2-methylaniline sulfate | 5 g |
| Sodium sulfite | 5 g |
| Hydroxylamine sulfate | 2 g |
| Potassium carbonate | 30 g |
| Potassium hydrogencarbonate | 1.2 g |
| Potassium bromide | 1.2 g |
| Sodium chloride | 0.2 g |
| Trisodium nitrilotriacetate | 1.2 g |
| Water to make | 1 liter (pH 10.1) |
| Bleaching Solution | |
| Water | 800 ml |
| Iron (III) ammonium ethylenediaminetetraacetate | 100 g |
| Disodium ethylenediaminetetraacetate | 10 g |
| Potassium bromide | 150 g |
| Acetic acid | 10 g |
| Water to make | 1 liter (pH 6.0) |
| Fixing Solution | |
| Water | 800 ml |
| Ammonium thiosulfate | 150 g |
| Sodium thiosulfite | 10 g |
| Sodium hydrogensulfite | 2.5 g |
| Water to make | 1 liter (pH 6.0) |
| Fixing Solution | |
| Water | 800 ml |
| Formalin (37%) | 5 ml |
| Driwel | 3 ml |
| Water to make | 1 liter |

Photographic properties thus obtained are tabulated in Table 1.

TABLE 1

| Sample No. | Developing Agent or Its Precursor | Fog | Gamma | Relative* Sensitivity | Maximum Color Density |
|---|---|---|---|---|---|
| 1 | — | 0.12 | 0.62 | 100 | 1.38 |
| 2 | D-1 | 0.21 | 0.84 | 80 | 1.50 |
| 3 | D-2 | 0.24 | 0.83 | 82 | 1.58 |
| 4 | D-3 | 0.19 | 0.78 | 89 | 1.57 |
| 5 | D-4 | 0.17 | 0.84 | 98 | 1.60 |
| 6** | (1) | 0.13 | 0.75 | 128 | 1.58 |
| 7** | (11) | 0.12 | 0.80 | 118 | 1.57 |
| 8** | (4) | 0.13 | 0.77 | 129 | 1.58 |
| 9** | (9) | 0.13 | 0.75 | 122 | 1.53 |
| 10** | (7) | 0.12 | 0.71 | 119 | 1.55 |

*Relative sensitivity: numerical values of reciprocals of exposure amounts required for attaining an effective density of 0.2 excluding fog, taking that of additive-free sample 1 as 100.
**Present invention It is clear from Table 1 that samples 6 to 10 containing the developing agent precursors of the present invention showed increased gamma, sensitivity and color density without an increase in fog.

The magenta coupler and developing agents used are as follows:

Magenta Coupler $C_{p-1}$

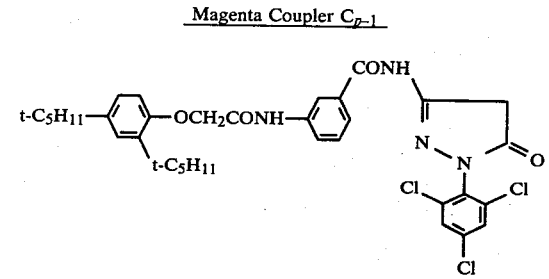

Developing Agent

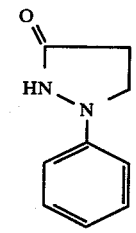

D-1

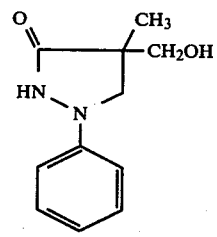

D-2

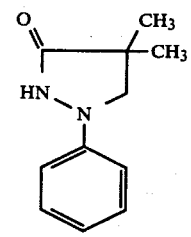

D-3

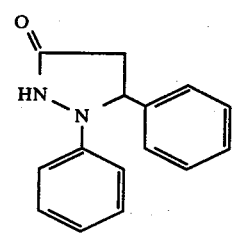

D-4

EXAMPLE 2

In order to evaluate the effectiveness of the developing agent precursors of the present invention in comparison with control compounds, developing agents or precursors thereof given in Table 2 were coated on paper supports laminated on both sides with polyethylene in the same manner as in Example 1 to prepare samples 11 to 19.

(1) Emulsion Layer

Negative type silver chlorobromide emulsion (grain size: 0.7μ) (silver: $5.12 \times 10^{-3}$ mol/m$^2$)
Yellow coupler $C_{p-2}$ ($8.53 \times 10^{-4}$ mol/m$^2$)
Developing agent or its precursor ($5.12 \times 10^{-4}$ mol/m$^2$)
Gelatin (1.35 g/m$^2$)

(2) Protective Layer
Gelatin (1.30 g/m$^2$)
2,4-Dichloro-6-hydroxy-s-triazine sodium salt (50 mg/m$^2$)

These films were left for 14 hours at 40° C. and 70% RH, then imagewise exposed for conducting sensitometry and subjected to the following color development processing.

| Color Development Processing | Time (min) | Temperature (°C.) |
|---|---|---|
| 1. Color development | 2 | 33 |
| 2. Bleach-fixing | 1.50 | 33 |
| 3. Washing with water | 2.50 | 25–30 |

The compositions of processing solutions used in the color development processing steps are as follows:

| Color Developing Solution | |
|---|---|
| Benzyl alcohol | 15 ml |
| Diethylene glycol | 8 ml |
| Ethylenediaminetetraacetic acid | 5 g |
| Sodium sulfite | 2 g |
| Anhydrous potassium carbonate | 30 g |
| Hydroxylamine sulfate | 3 g |
| Potassium bromide | 0.6 g |
| 4-Amino-N—ethyl-N—(β-methanesulfonamido-ethyl)-m-toluidine 3/2 sulfate monohydrate | 5 g |
| Water to make | 1 liter |
| | pH: adjusted to 10.20 |
| Bleach-Fixing Solution | |
| Ethylenediaminetetraacetic acid | 2 g |
| Iron (III) ethylenediaminetetraacetate | 40 g |
| Sodium sulfite | 5 g |
| Ammonium thiosulfate | 70 g |
| Water to make | 1 liter |

The results on photographic properties thus obtained are tabulated in Table 2.

TABLE 2

| Sample No. | Developing Agent or Its Precursor | Fog | Gamma | Relative Sensitivity |
|---|---|---|---|---|
| 11 | — | 0.06 | 2.17 | 100 |
| 12 | D-3 | 0.13 | 2.26 | 115 |
| 13 | D-2 | 0.11 | 2.25 | 118 |
| 14 | D-5 | 0.08 | 2.42 | 80 |
| 15 | D-4 | 0.09 | 2.28 | 120 |
| 16* | (8) | 0.06 | 2.15 | 127 |
| 17* | (10) | 0.06 | 2.17 | 123 |
| 18* | (13) | 0.06 | 2.22 | 119 |
| 19* | (12) | 0.06 | 2.18 | 121 |

*Present invention

It is seen from Table 2 that, when developing agents were added as such, some caused fogging, though they attained sensitization to some extent, and others caused desensitization, though they did not increase fog, and that the compounds of the present invention attained sensitization without an increase in fog.

The yellow coupler and the developing agents used are as follows:

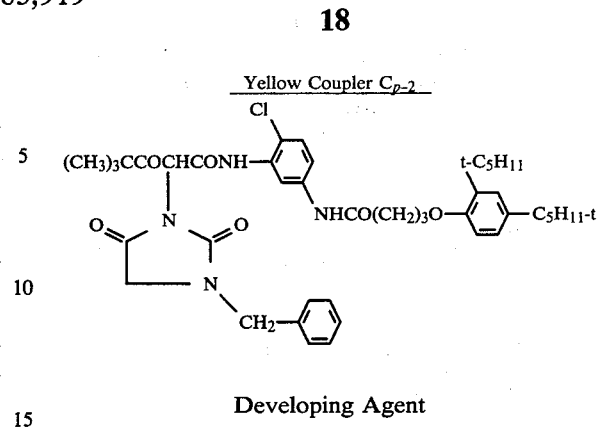

Yellow Coupler $C_{p-2}$

Developing Agent

D-2 and D-4 are the same compounds as described in Example 1.

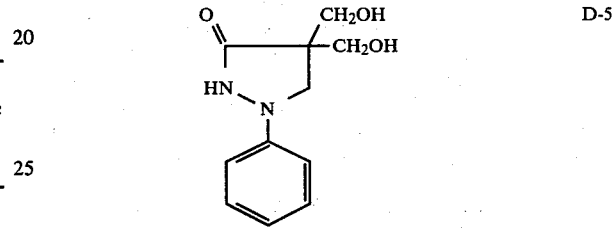

D-5

EXAMPLE 3

The following light-sensitive sheet and image-receiving sheet were prepared.

Light-Sensitive Sheet:
On a polyethylene-laminated paper were coated the following emulsion layer and the protective layer to prepare light-sensitive sheets 1 to 7 as shown in Table 3. The developing agents or the precursors thereof were dissolved in methanol and added to the emulsion.

(1) Emulsion Layer
Silver iodobromide emulsion containing 4% silver iodide (silver: $9.2 \times 10^{-3}$ mol/m$^2$)
Developing agent or its precursor ($1.0 \times 10^{-6}$ mol/m$^2$)
Gelatin (1.50 g/m$^2$)

(2) Protective Layer
Gelatin (1.0 g/m$^2$)
2,4-Dichloro-6-hydroxy-s-triazine sodium salt (10 mg/m$^2$)

Image-Receiving Sheet:
Polyethylene-laminated paper having a 6 μm cellulose triacetate layer was dipped for 1 minute in an alkaline hydrolyzing solution containing silver-depositing nuclei to prepare common diffusion transfer process image-receiving sheets.

The alkaline hydrolyzing solution was prepared as follows. 0.1 g of nickel nitrate was dissolved in 2 ml of water and added to 100 ml of glycerin and, under vigorous stirring, a solution of 1 g of sodium sulfide dissolved in 2 ml of water was further added thereto to prepare a dispersion of silver-depositing nickel sulfide nuclei. 20 ml of the dispersion was added to a 1,000 ml of a water/methyl alcohol (1/1) solution having dissolved therein 80 g of sodium hydroxide to prepare an alkaline hydrolyzing solution containing silver-depositing nuclei.

The aforesaid light-sensitive sheets 1 to 7, having or not having been kept under incubating condition (60° C.) for 3 hours, were respectively imagewise exposed for conducting sensitometry. The following processing solution was spread between each of the light-sensitive sheets and the aforesaid image-receiving sheet in a thickness of 0.1 mm to conduct diffusion transfer development.

| Processing Solution | |
|---|---|
| Potassium hydroxide (40% aq. soln.) | 323 ml |
| Titanium dioxide | 3 g |
| Hydroxyethyl cellulose | 79 g |
| Zinc oxide | 9.75 g |
| N,N—Bismethoxyethylhydroxylamine | 75 g |
| Triethanolamine (45% aq. soln.) | 17.14 g |
| Tetrahydropyrimidinethione | 0.4 g |
| 2,4-Dimercaptopyrimidine | 0.35 g |
| Uracil | 90 g |
| Water | 1,193 ml |

Optical densities of the thus obtained transferred silver images were measured, and reciprocals of exposure amounts required for attaining an optical density of 0.7 were used for indicating sensitivities. The sensitivities are given in Table 3 as relative values, taking that of the additive-free sample (light-sensitive sheet No. 1) not having been subjected to the incubation as 100.

TABLE 3

| Sample Light-Sensitive Sheet No. | Developing Agent or Its Precursor | Before Incubation Sensitivity | Before Incubation Transferred Ag Density | After Incubation Sensitivity | After Incubation Transferred Ag Density |
|---|---|---|---|---|---|
| 1 | — | 100 | 1.60 | 90 | 1.45 |
| 2 | D-3 | 145 | 1.60 | 120 | 0.80 |
| 3 | D-1 | 130 | 1.54 | 100 | 0.62 |
| 4 | D-6 | 152 | 1.55 | 105 | 0.73 |
| 5* | (9) | 120 | 1.57 | 115 | 1.45 |
| 6* | (2) | 130 | 1.63 | 135 | 1.49 |
| 7* | (14) | 115 | 1.62 | 115 | 1.42 |

*Present invention

As is shown in Table 3, samples 2 to 7 containing developing agents or their precursors showed higher sensitivities than that of sample No. 1 not containing them. However, samples 2 to 4 containing developing agents underwent serious reduction in transferred silver density under the incubation condition. On the other hand, samples 5 to 7 containing the compounds of the present invention underwent only a slight reduction in transferred silver density while maintaining their sensitivity at a high level.

The developing agent precursors used are as follows. D-1 and D-3 are the same as used in Example 1.

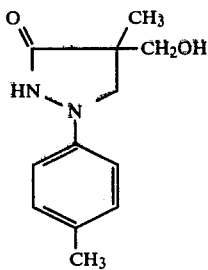

D-6

EXAMPLE 4

In order to evaluate the effectiveness of the developing agent precursors of the present invention in comparison with control (comparative) compounds, developing agents or precursors thereof given in Table 4 were dissolved in dibutyl phthalate and ethyl acetate to emulsify, and added to emulsions, followed by coating each of the emulsions on a subbed cellulose triacetate film support to prepare samples 20 to 24. The amounts of respective substances coated were indicated in parentheses as numerical values in terms of g/m$^2$ or mol/m$^2$.

(1) Emulsion Layer
  Negative type silver iodobromide solution (grain size: 0.6μ) (silver: $2.5 \times 10^{-2}$ mol/m$^2$)
  Gelatin (2.50 g/m$^2$)

(2) Protective Layer
  Developing agent or its precursor ($1.33 \times 10^{-3}$ mol/m$^2$)
  Gelatin (1.30 g/m$^2$)
  2,4-Dichloro-6-hydroxy-s-triazine sodium salt (50 mg/m$^2$)

These films were left for 14 hours at 40° C. and 70% RH, then imagewise exposed for conducting sensitometry and subjected to the following black-and-white development.

| Black-and-White Developing Step | Time (min) | Temperature (°C.) |
|---|---|---|
| 1. Black-and-white development | 4 | 20 |
| 2. Stopping | 1 | " |
| 3. Fixing | 10 | " |
| 4. Washing with water | 10 | " |

The compositions of processing solutions used in the black-and-white processing steps are as follows:

| Black-and-White Developing Solution | |
|---|---|
| Water | 800 ml |
| 1-Phenyl-3-pyrazolidinone (phenidone) | 0.2 g |
| Hydroquinone | 12.0 g |
| Sodium carbonate | 79.0 g |
| Sodium sulfite | 45 g |
| Potassium bromide | 1.9 g |
| Water to make | 1 liter |
| Stopping Bath | |
| Acetic acid aqueous solution (1.5%) | |
| Fixing Solution | |
| Water | 800 ml |
| Sodium thiosulfate | 100 g |
| Water to make | 1 liter |

Photographic properties thus obtained are tabulated in Table 4.

TABLE 4

| Sample No. | Developing Agent or Its Precursor | Fog | Gamma | Relative* Sensitivity | Maximum Sensitivity |
|---|---|---|---|---|---|
| 20 (Control) | — | 0.04 | 0.98 | 100 | 1.65 |
| 21** | D-1* | 0.12 | 1.24 | 88 | 1.66 |
| 22** | D-2* | 0.10 | 1.21 | 109 | 1.63 |
| 23*** | (1) | 0.05 | 1.18 | 117 | 1.62 |
| 24*** | (8) | 0.04 | 1.16 | 112 | 1.67 |

*Same as used in Example 1
**Comparison
***Present invention

Table 4 clearly shows that samples 23 and 24 containing the precursors of the present invention showed increased gamma and sensitivity while scarcely increasing fog.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material containing at least one compound represented by the following general formula (I):

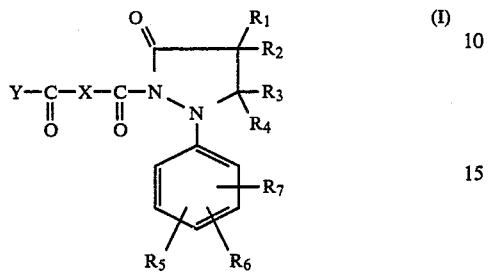

wherein $R_1$ and $R_2$ each independently represent a hydrogen atom or an alkyl group; $R_3$ and $R_4$ each independently represent a hydrogen atom, an alkyl group, an alkoxycarbonyl group or an aryl group; $R_5$, $R_6$ and $R_7$ each independently represent a hydrogen atom, a halogen atom, an alkyl group, an alkoxy group, an aryl group, a carbonamido group or a sulfonamido group; X represents a divalent linkage group represented by the following general formula (II) or (III):

wherein $R_8$ represents a hydrogen atom, an alkyl group, an alkenyl group, an aryl group, a halogen atom, an alkoxy group or an alkylthio group; $R_9$ and $R_{10}$ each independently represent a hydrogen atom, a halogen atom, an alkyl group or an aryl group, provided $R_9$ and $R_{10}$ may jointly form a benzene ring; and n represents an integer of 2 or 3; and Y represents —OH,

or $R_{13}$ wherein $R_{11}$ represents a hydrogen atom, an aryl group or an alkyl group; $R_{12}$ represents a hydrogen atom or an acyl group; and $R_{13}$ represents a hydrolyzable group.

2. A silver halide photographic light-sensitive material as claimed in claim 1, wherein $R_1$ and $R_2$ each independently represent a hydrogen atom or an alkyl group containing 1 to 18 carbon atoms; and $R_3$ and $R_4$ each independently represent a hydrogen atom, an alkyl group containing 1 to 12 carbon atoms, an alkoxycarbonyl group containing up to 13 carbon atoms, or an aryl group containing up to 18 carbon atoms.

3. A silver halide photographic light-sensitive material as claimed in claim 1, wherein:

$R_1$ and $R_2$ each independently represent a hydrogen atom, a methyl group, an ethyl group, a hydroxymethyl group, a hydroxyethyl group, a chloromethyl group, an acetoxymethyl group, a benzoyloxymethyl group, or a tetradecanoyloxymethyl group;

$R_3$ and $R_4$ each independently represent a hydrogen atom, a methyl group, an ethyl group, a methoxycarbonyl group, an ethoxycarbonyl group, a hexyloxycarbonyl group, a phenyl group, a 4-methoxyphenyl group, a 2-methoxyphenyl group, a 2-hydroxyphenyl group, a 4-chlorophenyl group, or a 3-butoxyphenyl group;

$R_5$, $R_6$ and $R_7$ each independently represent a hydrogen atom, a fluorine atom, a chlorine atom, a bromine atom, a methyl group, an ethyl group, a dodecyl group, a methoxy group, an ethoxy group, a butoxy group, a hexadecyloxy group, a methoxyethoxy group, a butoxyethoxy group, a phenyl group, a p-tolyl group, an acetamido group, or a methanesulfonamido group;

$R_8$ represents a hydrogen atom, a methyl group, a dodecyl group, an octadecenyl group, a phenyl group, a 4-dodecylphenyl group, a fluorine atom, a chlorine atom, a bromine atom, a methoxy group, a dodecyloxy group, a methylthio group, or a dodecylthio group;

$R_9$ and $R_{10}$ each independently represent a hydrogen atom, a fluorine atom, a chlorine atom, a bromine atom, a methyl group, an octyl group, a phenyl group, or a 4-methoxyphenyl group;

$R_{11}$ represents a hydrogen atom, a phenyl group, a 4-methoxyphenyl group, a 2-chlorophenyl group, a 4-methylphenyl group, a methyl group, an isopropyl group, or a dodecyl group;

$R_{12}$ represents a hydrogen atom, an acetyl group, a benzoyl group, or a p-nitrobenzoyl group; and $R_{13}$ represents a phenoxy group, a 4-chlorophenoxy group, a 4-nitrophenoxy group, a 2,4-dinitrophenoxy group, a 2,2,2-trifluoroethoxy group, a 2-cyanoethoxy group, a 2,2,2-trichloroethoxy group, or a 2,2-dichloroethoxy group.

4. A silver halide photographic light-sensitive material as claimed in claim 1, wherein the compound of the general formula (I) is selected from the following compounds (1) to (16):

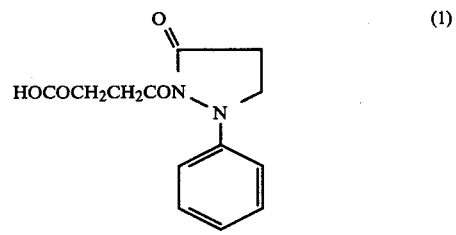

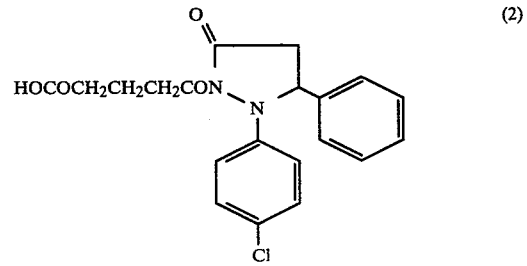

-continued
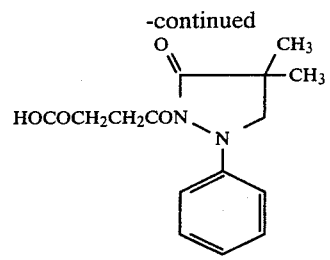 (3)
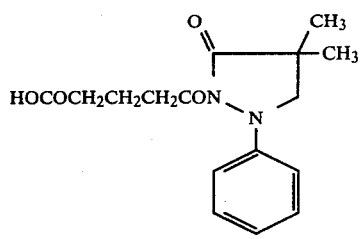 (4)
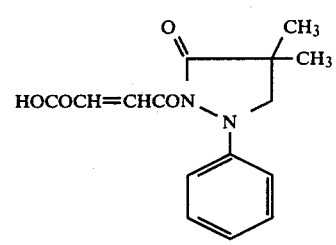 (5)
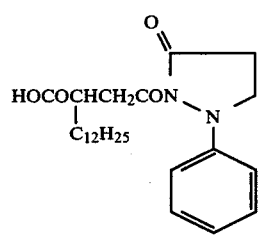 (6)
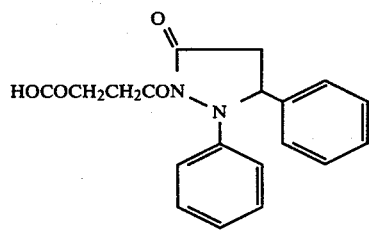 (7)
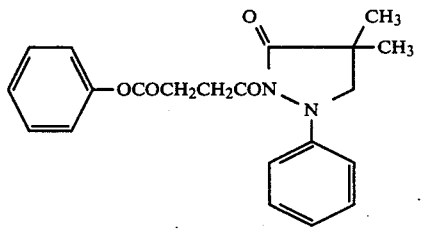 (8)
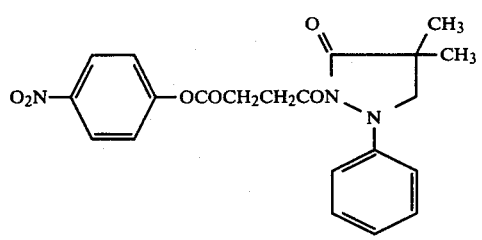 (9)
-continued
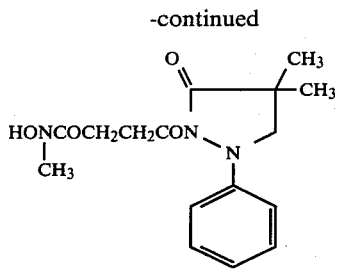 (10)
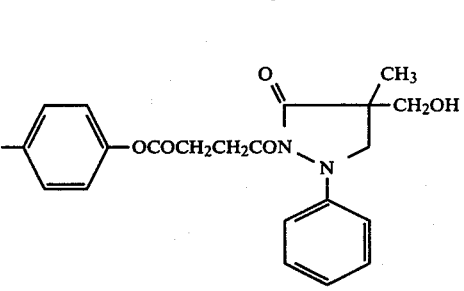 (11)
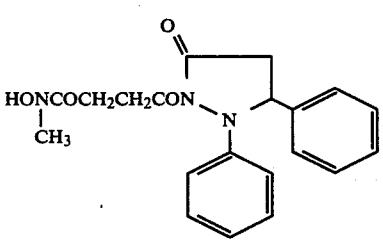 (12)
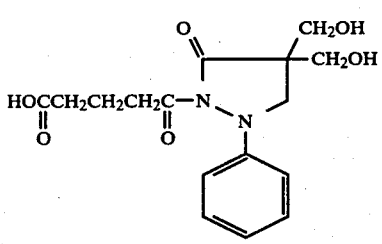 (13)
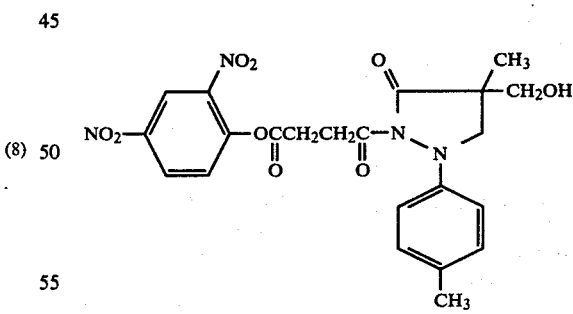 (14)
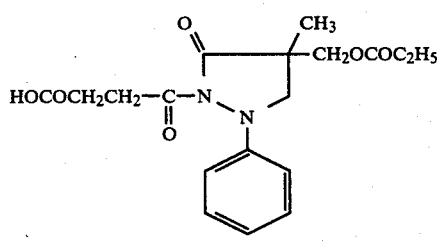 (15)

-continued (16)

[Structure: 1-phenyl-2-(HOCOCH₂CH₂CON)-4-(2-methoxybenzyl)-pyrazolidin-3-one]

5. A silver halide photographic light-sensitive material as claimed in claim 1, wherein the compound of the general formula (I) is present in an amount in the range of $10^{-9}$ mol to $10^{-1}$ mol per m$^2$ of the silver halide photographic light-sensitive material.

6. A silver halide photographic light-sensitive material as claimed in claim 5, wherein the compound of the general formula (I) is present in an amount in the range of $10^{-7}$ mol to $10^{-2}$ mol per m$^2$ of the silver halide photographic light-sensitive material.

7. A color photographic light-sensitive material, comprising the silver halide photographic light-sensitive material as claimed in claim 1.

8. A color diffusion transfer photograhic light-sensitive material, comprising the silver halide photographic light-sensitive material as claimed in claim 1.

9. A black-and-white photographic light-sensitive material comprising the silver halide photographic light-sensitive material as claimed in claim 1.

* * * * *